United States Patent [19]

Chupp

[11] 4,188,342

[45] Feb. 12, 1980

[54] ORTHO-BROMINATION OF ORTHO-ALKYLATED ANILINES

[75] Inventor: John P. Chupp, Kirkwood, Mo.

[73] Assignee: Monsanto Company, St. Louis, Mo.

[21] Appl. No.: 5,057

[22] Filed: Jan. 22, 1979

[51] Int. Cl.$^2$ ............... C07C 87/28; C07C 91/06; C07C 91/16; C07C 91/40
[52] U.S. Cl. .................... 260/578; 260/573; 260/574; 260/575; 260/577
[58] Field of Search ............... 260/578, 573, 574, 575, 260/577

[56] References Cited

PUBLICATIONS

Kleinschmidt et al., Chem. Absts., vol. 70, 114730p, (1969).
Mori, et al., Chem. Absts., vol. 76, 99375c, (1972).
Hoi, et al., J. Chem. Soc., pp. 2815–2821, (1958).

*Primary Examiner*—John F. Niebling
*Attorney, Agent, or Firm*—William I. Andress; Donald W. Peterson

[57] ABSTRACT

The disclosure herein pertains to o-brominated-o-alkylated anilines and a process for the preparation thereof. The substituted anilines prepared herein are useful as intermediates in the preparation of herbicidal 2-haloacetanilides.

10 Claims, No Drawings

ORTHO-BROMINATION OF ORTHO-ALKYLATED ANILINES

BACKGROUND OF THE INVENTION

The invention herein pertains to the field of o-brominated-o-alkylated anilines and processes for the preparation thereof.

DESCRIPTION OF THE PRIOR ART

The prior art relevant to the process of this invention discloses the use of N-chlorosuccinimide (NCS) and N-bromosuccinimide (NBS), respectively, as chlorinating and brominating agents in inert solvents such as ethylene dichloride, carbon tetrachloride, chloroform and hydrocarbons, e.g., toluene and benzene. These hologenation systems (known as the Wohl-Ziegler reaction when applied to NBS) have been used by prior workers on a variety of substrates including aliphatic and alicyclic olefins, isoprenoids, steroids, conjugated and unconjugated polyolefins, carbonyl compounds, compounds with functional groups alpha or beta to a double bond, aromatic hydrocarbons, amines and heterocyclic systems. See Encyclopedia of Chemical Technology (Ed. R. E. Kirk and D. F. Othmer), Vol. 7, . 352, 353 (1951).

The halogenation of various substrate materials with NCS and NBS has been shown to be, in many instances, very much unpredictable as to product and by-product ratios obtained. Various parameters influencing the halogenation reaction include the particular substrate being halogenated, the nature of the reaction medium and its pH level and the use of certain catalysts. For example, F. L. Lambert, et al, (Journal of Organic Chemistry [J.O.C.], Vol. 30, . 304–306 [1965]) describe the use of NCS and NBS in aqueous sulfuric acid to halogenate various aromatic compounds such as benzene, toluene, chlorobenzene and nitrobenzene to obtain a mixture of nuclear-halogenated o, m and p isomers. The use of NCS to chlorinate anilines and N-alkylanilines has led to the production of p-chlorinated aniline or mixtures of o- and p-chlorinated aniline; see, e.g., Ng. Ph. Buu-Hoi, et al, Chem. Abs. 53, 358 (1959); R. S. Neale, et al, J.O.C. 29, pp. 3390–93; D. F. Paul, et al, Ibid. 41, No. 19, pp. 3170–3175 (1976) and T. H. Chao, et al, Ibid., 26 pp. 1079–81 (1961). Other workers have described the bromination with bromine, N-bromoacetamide or NBS of phenols to obtain the various brominated isomers thereof in varying ratios, including the production of o-bromophenol exclusively (at temperatures of about −70° C. in the presence of a strong basic aliphatic amine); see D. E. Pearson, et al, Ibid, 32, pp. 2358–2360 (1967).

The use of NBS as a brominating agent for aromatic amines and acetanilides has led to bromination of side chain substituents, p-bromination alone or o- and p-dibromination and/or mixtures of o- and p-brominated products. Thus, BuuHoi, et al, op. cit., found that bromination of N-acetyl-3-chloroacetanilide with NBS in CCl₄ followed by deacetylation with HCl led to 4-bromo-3-chloroaniline; similarly prepared were 4-bromo-2-methylaniline and 4-bromo-3-fluoroaniline, see also Kleinschmidt, et al, Chem. Abs. 70, p. 296 (1969). Mathur, et al, (Academic Press. pp. 54, 56 (1975) found that the bromination of aniline gave 2,4,6-tribromoaniline and that bromination of the toluidines and N-alkylanilines gave inconsistent results leading to side-chain and nuclear bromination. The only known o-bromination of anilines (without concomitant m- or p-bromination) occurs when the p-position is blocked with some functional group. See, e.g., Kleinschmidt, op. cit. and Kleinschmidt, et al, Chem. Abs. 72, paragraph 89632q (1970).

It is, therefore, an object of this invention to provide a process for preparing brominated o-alkyl anilines and N-substituted anilines predominating in o-brominated isomers, minor amounts of p-brominated and mixed o- and p-brominated products or exclusively the o-brominated isomer.

SUMMARY OF THE INVENTION

This invention relates to a process for the preparation of compounds having the formula

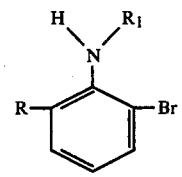

which comprises reacting a compound of the formula

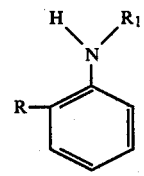

with a compound of the formula

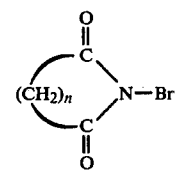

in an inert solvent at temperatures within the range of −25° C. to 125° C., wherein in the above formulae R is $C_{1-6}$ alkyl, $R_1$ is hydrogen, $C_{1-6}$ alkyl or an alkoxyalkyl radical of the formula—$(CR_2R_3)_mOR_4$ wherein $R_2$ and $R_3$ are hydrogen or $C_{1-3}$ alkyl, m is 2, 3 or 4 and $R_4$ is $C_{1-4}$ alkyl and n is an integer from 1 to 8 inclusive.

In preferred embodiments the above process is conducted at room temperature using N-bromosuccinimide as the brominating agent. Alternative brominating agents include homologous N-bromoimides of dibasic acids such as malonic, glutaric, adipic, pimelic, suberic, azelaic and sebacic. Other brominating agents include N-bromophthalimide, N-bromoacetamide and N-bromocaprolactam.

Suitable solvents for use in the process of this invention include inert aliphatic and aromatic hydrocarbon or halogenated hydrocarbons such as the halogenated alkanes, e.g., $CCl_4$, $CHCl_3$, $CH_2Cl_2$, $C_2H_3Cl_3$, etc., naphtha, benzene, halogenated benzenes, toluene, the xylenes, etc.

DETAILED DESCRIPTION OF THE INVENTION

Example 1

To 150 g (1.4 mol) of o-toluidine in 4 liters of benzene was added at once 250 g (1.4 mol) of N-bromo-succinimide. The mixture was stirred 6 hours. GLC showed the run to be complete; the contents were very dark. Analysis of the mixture showed 6% of starting aniline, 69% of 2-bromo-o-toluidine product, 22% of 4-bromo-o-toluidine and 4% of 2,4-dibromo-o-toluidine. The benzene was stripped leaving 285 g of an oil which was taken up in pentane to which ice and 40 g of acetic anhydride were added. The mixture was filtered then the formed layers separated. The pentane after separation from the water layer was removed in vacuo leaving an oil which was vacuum distilled at 83° C. (1.5 mm) to give 48.4 g (19% yield) of the 2-bromo-o-toluidine and upon repetition of the vacuum distillation at 66° C. (0.5 mm) obtained 36.4 g (14% yield) of the 2-bromo-o-toluidine, a colorless oil.

Example 2

O-Ethylaniline (168 g, 1.4 mol) in 1 l. toluene was charged to a 2 l., 4-necked flask with an Erlenmeyer flask attached with gooch tubing for introduction of NBS. Exit of condenser protected from atmospheric moisture by drying tube. The flask was cooled to −78° C., and NBS added all at once, then mixture with stirring allowed to warm up slowly. Material stirred four hours, and allowed to stand overnight, succinimide filtered off. Glc showed a mixture of brominated 6-ethylaniline isomers. In order to separate the isomeric o- and p- monobrominated anilines, 102 g acetic anhydride added to the toluene solution and solid filtered off, then filtrate filtered again. Filtrate washed with water, dried over MgSO4, then solvent removed under vaccum, with glc showing only 2-bromo-6-ethylaniline, bp 85°–95° C./0.35 mm, 60 g.

| Anal. for $C_8H_{10}BrN$ (%) : | Element | Calc'd | Found |
|---|---|---|---|
| | C | 48.02 | 48.11 |
| | H | 5.04 | 5.10 |
| | N | 7.00 | 6.98 |

In two other runs comparable to the above, the product distribution showed, respectively, 60% o-bromo and 40% p-bromo isomer and 67% o-bromo and 33% p-bromo isomer.

Example 3

To o-isopropylaniline in 4 l. benzene (0.74 mol, 100 g) was added 131.7 g (0.74 mol) NBS all at once. There was an exotherm to 35° C. Material was stirred two hours, then let stand overnight. The volume was reduced by three-quarters, and solid removed by filtration. Benzene was then removed from the filtrate, pentane added with ice, followed by 40 ml acetic anhydride. After ca. 15 minutes, solid was filtered off, pentane solution separated from filtrate, washed with ammonia water. After evaporation of pentane, oil was distilled 83° C. (0.25 mm) to give 64.5 g of 2-bromo-6-isopropylaniline.

| Anal. for $C_9H_{12}BrN$ (%) : | Element | Calc'd | Found |
|---|---|---|---|
| | C | 50.49 | 50.45 |
| | H | 5.65 | 5.65 |
| | N | 6.54 | 6.53 |

The solid was recrystallized from isopropanol to give 15.5 g 4'-bromo-2'-isopropyl acetanilide.

Example 4

To o-t-butylaniline (65.6 g, 0.44 mol) in 3 l. of benzene was added 78.3 g (0.44 mol) NBS all at once. Contents turned from pick to yellow with small exotherm to 30° C.; color remained overnight, although with other lower-o-alkyl-anilines, color would darken. Glc showed no starting material, with over 50% desired o-bromo-6-t-butylaniline. Benzene was removed under vacuum, residue was taken up in pentane and filtered. Ice was added to pentane, followed by 20 ml acetic anhydride with stirring. The solid was filtered off, and after pentane evaporation from filtrate, oil was distilled, bp 82° C. (0.05 mm) to give 40.9 g 2-bromo-6-t-butylaniline.

| Anal. for $C_{10}H_{14}BrN$ (%) : | Element | Calc'd | Found |
|---|---|---|---|
| | C | 52.65 | 52.68 |
| | H | 6.19 | 6.18 |
| | N | 6.14 | 6.14 |

The solid was recrystallized twice from isopropanol, to give 4'-bromo-2'-t-butyl acetanilide.

In a manner similar to that described in the preceding examples, analogous o-brominated products having N-alkyl and N-alkoxy substituents are prepared. As exemplary compounds of such structure are mentioned the following:

N-methyl-2-bromo-6-methylaniline
N-ethyl-2-bromo-6-ethylaniline
N-propyl-2-bromo-6-propylaniline
N-isopropyl-2-bromo-6-isopropylaniline
N-n-butyl-2-bromo-6-n-butylaniline
N-t-butyl-2-bromo-6-t-butylaniline
N-t-butyl-2-bromo-6-methylaniline
N-pentyl-2-bromo-6-methylaniline
N-n-butyl-2-bromo-6-methylaniline
N-isopropyl-2-bromo-6-methylaniline
N-methyl-2-bromo-6-pentylaniline
N-methoxyethyl-2-bromo-6-methylaniline
N-ethoxyethyl-2-bromo-6-methylaniline
N-propoxyethyl-2-bromo-6-methylaniline
N-isopropoxyethyl-2-bromo-6-methylaniline
N-n-butoxyethyl-2-bromo-6-methylaniline
N-t-butoxyethyl-2-bromo-6-methylaniline
N-2-ethoxy-1-methylethyl-2-bromo-6-methylaniline
N-2-ethoxy-2-methylethyl-2-bromo-6-methylaniline
N-2-ethoxy-1-ethylethyl-2-bromo-6-methylaniline
N-3-methoxypropyl-2-bromo-6-methylaniline
N-4-methoxybutyl-2-bromo-6-methylaniline The 2-bromo-6-alkylanilines produced according to the process of this invention are useful as intermediates in the preparation of 2-haloacetanilide derivatives which are known herbicides. For example, these anilines may be directly haloacetylated with a haloacetyl halide or anhydride thereof to the corresponding 2-haloacetanilide of the type described in Belgian Pat. No.

622,131. Alternatively, the 2-bromo-6-alkyl anilines of this invention may be converted to herbicidal 2-haloacetanilides as described in Belgian Pat. No. 852,621 by first reacting the aniline with formaldehyde to obtain the corresponding substituted phenylazomethine which is then haloacetylated to produce the corresponding N-halomethyl derivatives which when reacted with the desired alcohol produces the corresponding N-alkoxymethyl-2-haloacetanilide as exemplified in Examples 5 and 6.

Example 5

The product of Example 1, i.e., 2-bromo-o-toluidine, 17.4 g (0.094 mol) in a 100 ml flask with thermometer well, together with 10 g paraformaldehyde $(CH_2O)_x$, 2 ml of triethylamine (TEA) and 3 drops of commerically available stabilizer to inhibit polymerization of the azomethine intermediate was heated at 100° C. for 2 hours under nitrogen. The temperature was raised to 110° C. Contents stayed light in color. Held at 110° C. for 2 hours. Chlorobenzene was added and temperature kept at 110° C. another hour then allowed to cool. Filtered $(CH_2O)_x$ and chloroacetylchloride (CAC) 11.3 g (0.1 mol) added to filtrate with shaking. After one hour 100 ml of isopropanol was added and held at 40° C. one hour. Stood over weekend. Filtered off-white solid and volatiles removed in vacuo. Residue put through silica gel with 3:2 hexane/ether. Fraction 3 held product which was stripped and vacuum distilled leaving an oil bp 135° C. at 0.25 mm Hg weighing 3.5 g.

| Anal. for $C_{13}H_{17}BrClNO_2$ (%): | Element | Calc'd | Found |
|---|---|---|---|
| | C | 46.66 | 46.46 |
| | H | 5.12 | 5.15 |
| | N | 4.19 | 4.15 |

The product was identified as 2-bromo-6'-methyl-N-isopropoxymethyl-2-chloroacetanilide.

Example 6

Fifty nine grams (0.276 mol) of 2-bromo-6-isopropylaniline (the produce of Example 3), 15 g $(CH_2O)_x$, 2 ml TEA and 4 drops of an azomethine depolymerization stabilizer were heated at 100° C. for 2 hours; water of reaction being caught in a Dean Stark trap. The temperature was raised to 110° C. for one hour and 2-bromo-6-isopropylphenyl azomethine distilled through a heated tube into chlorobenzene into which was then added 18 g CAC to produce the corresponding 2'-bromo-6'-isopropyl-N-(chloromethyl)-2-chloroacetanilide. One hundred ml of methanol was added and the temperature held at 40° C. overnight. The volatiles were then stripped under high vacuum leaving dark oil residue. Glc showed very little secondary anilide (~5%). The oil was then put through silica gel with 3:2 hexane/ether eluant. Fractions 2–4 held the product and Fraction 5 contained product and secondary anilide. Fractions 2–4 were combined and again put through silica gel to remove the secondary anilide. Fractions 2 and 3 were vacuum distilled leaving 16 g (34.6% yield) of product, bp 135° C. at 0.25 mm.

| Anal. for $C_{13}H_{17}BrClNO_2$ (%): | Element | Calc'd | Found |
|---|---|---|---|
| | C | 46.66 | 46.72 |
| | H | 5.12 | 5.16 |
| | N | 4.19 | 4.16 |

The product was identified as 2'-bromo-6'-isopropyl-N-(methoxymethyl)-2-chloroacetanilide.

Although this invention has been described with respect to specific modifications, the details thereof are not to be construed as limitations, since it will be apparent that various equivalents and modifications may be resorted to without departing from the spirit and scope of the invention.

I claim:

1. Process for the preparation of compounds having the formula

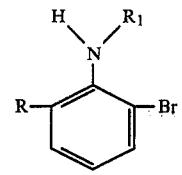

which comprises reacting a compound of the formula

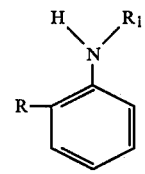

with a compound of the formula

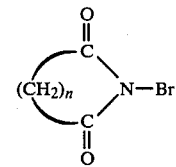

in an inert solvent at temperatures within the range of 25° C. to 125° C., wherein in the above formulae
R is $C_{1-16}$ alkyl,
$R_1$ is hydrogen, $C_{1-6}$ alkyl or an alkoxyalkyl radical of the formula $-(CR_2R_3)_mOR_4$ wherein $R_2$ and $R_3$ are hydrogen or $C_{1-3}$ alkyl, m is 2, 3 or 4 and $R_4$ is $C_{1-4}$ alkyl and
n is an integer from 1 to 8 inclusive.

2. Process according to claim 1 wherein said reaction is conducted at room temperature.

3. Process according to claim 2 wherein said compound of Formula III is N-bromosuccinimide.

4. Process according to claim 3 wherein $R_1$ is a $C_{1-6}$ alkyl radical.

5. Process according to claim 3 wherein $R_1$ is an alkoxyalkyl radical having the formula $-(CR_2R_3)_mOR_4$ wherein $R_2$ and $R_3$ are hydrogen or $C_{1-4}$ alkyl, m is 2, 3 or 4 and $R_4$ is a $C_{1-8}$ alkyl.

6. Process according to claim 3 wherein $R_1$ is hydrogen.

7. Process according to claim 6 wherein R is methyl.

8. Process according to claim 6 wherein R is ethyl.

9. Process according to claim 6 wherein R is isopropyl.

10. Process according to claim 6 wherein R is t-butyl.

* * * * *

UNITED STATES PATENT AND TRADEMARK OFFICE
CERTIFICATE OF CORRECTION

PATENT NO. : 4,188,342
DATED : February 12, 1980
INVENTOR(S) : John P. Chupp

It is certified that error appears in the above—identified patent and that said Letters Patent is hereby corrected as shown below:

Claim 1, Column 6, line 45, "31 25°C" should read -- 25°C --.

Signed and Sealed this

Eighth Day of September 1981

[SEAL]

Attest:

GERALD J. MOSSINGHOFF

Attesting Officer     Commissioner of Patents and Trademarks